United States Patent
Wu

(10) Patent No.: US 10,168,269 B1
(45) Date of Patent: Jan. 1, 2019

(54) AEROSOL REAL TIME MONITOR

(71) Applicant: WUXI MAITONG SCIENTIFIC INSTRUMENT CO., LTD, Wuxi (CN)

(72) Inventor: Ruzheng Wu, Wuxi (CN)

(73) Assignee: WUXI MAITONG SCIENTIFIC INSTRUMENT CO., LTD., Wuxi (CN)

( * ) Notice: Subject to any disclaimer, the term of this patent is extended or adjusted under 35 U.S.C. 154(b) by 0 days.

(21) Appl. No.: 15/742,880

(22) PCT Filed: Feb. 26, 2016

(86) PCT No.: PCT/CN2016/074631
§ 371 (c)(1),
(2) Date: Jan. 8, 2018

(87) PCT Pub. No.: WO2017/133045
PCT Pub. Date: Aug. 10, 2017

(30) Foreign Application Priority Data

Feb. 6, 2016 (CN) .......................... 2016 1 0084385

(51) Int. Cl.
*G01N 21/00* (2006.01)
*G01N 15/06* (2006.01)
(Continued)

(52) U.S. Cl.
CPC ..... *G01N 15/0631* (2013.01); *G01N 15/0211* (2013.01); *G01N 21/6402* (2013.01); *G01N 21/6486* (2013.01); *G01N 2015/0693* (2013.01)

(58) Field of Classification Search
CPC .... G01J 3/02; G01J 3/513; G01J 3/51; G01N 15/1459; G01N 21/65
(Continued)

(56) References Cited

U.S. PATENT DOCUMENTS

2002/0113136 A1* 8/2002 Talley ................ G01N 15/0205
239/1
2003/0098422 A1 5/2003 Silcott et al.
2005/0134836 A1* 6/2005 Paldus ...................... G01J 3/44
356/73

FOREIGN PATENT DOCUMENTS

CN 2786619 Y 6/2006
CN 201083677 Y 7/2008
(Continued)

*Primary Examiner* — Md M Rahman
(74) *Attorney, Agent, or Firm* — Gokalp Bayramoglu

(57) ABSTRACT

A biological and non-biological aerosol real time monitor includes a laser light source assembly configured to emit a laser beam and generate a line-shaped laser spot at a particle excitation position of an air flow to be measured; a sealed photoelectric measurement chamber, wherein the laser light source assembly is assembled at a laser entrance port of the sealed photoelectric measurement chamber, the air flow intersects with the optical axis in the traveling direction of the laser beam-at the particle excitation position; a scattered light signal reflecting mirror and a fluorescence signal reflecting mirror bilaterally provided with a measurement point as the center which is formed by the intersection of the laser beam and the air flow; a scattered light signal detector and a fluorescence signal detector respectively mounted behind a center opening of the reflecting mirrors to detect a scattered light signal and a fluorescence signal.

13 Claims, 4 Drawing Sheets

(51) Int. Cl.
*G01N 21/64* (2006.01)
*G01N 15/02* (2006.01)

(58) Field of Classification Search
USPC .......................................................... 356/73
See application file for complete search history.

(56) References Cited

FOREIGN PATENT DOCUMENTS

| | | |
|---|---|---|
| CN | 101398367 B | 4/2011 |
| CN | 102135492 A | 7/2011 |
| CN | 205562341 U | 9/2016 |

\* cited by examiner

AEROSOL REAL TIME MONITOR

CROSS REFERENCE TO RELATED APPLICATIONS

This application is the national phase entry of International Application PCT/CN2016/074631, filed on Feb. 26, 2016, which is based upon and claims priority to Chinese Patent Application No. 201610084385.3, filed on Feb. 6, 2016, the entire contents of which are incorporated herein by reference.

TECHNICAL FIELD

The present invention relates to an apparatus for monitoring the cleanliness of air in real time, which can measure the concentration and particle size of dust particles and biological particles in the air.

BACKGROUND

In many industries, such as medicine, electronics, precision machinery, microbiology and so on, a high air cleanliness is required for the factory building or ward. Generally, there are two index systems for the cleanliness of a clean room. One is the number of particles per unit volume of air, and the other is the number of microorganisms per unit volume of air. Moreover, for the first index, a laser airborne particle counter is usually used for the measurement. For the second index, instruments such as an airborne microbe sampler is usually used to sample the microorganisms in the air. Then, a cultivation and a count are performed. Finally, the number of microorganisms per unit volume of air is obtained based on the result by backstepping calculation.

For the detection of microbiological indicators in the air, the sampling & cultivation method is costly in terms of time and labor, especially when the measurement is performed frequently at multiple locations. In addition, since the sampling & cultivation method is not a real-time technical means, an on-line monitoring measurement cannot be realized. Moreover, the result is usually obtained after 24 hours or more. The time delay often brings trouble to the process such as quality control etc. during the production. To solve this problem, many new technologies are raised, and the most widely approved technology is the laser excitation biological fluorescence detection. Microorganisms in the air (mainly bacteria) generally contain fluorescent groups such as riboflavin, NADH, tryptophan, tyrosine, etc. When the microorganisms are exposed to the laser having a special wavelength, the microorganisms will emit the fluorescence having a specific wavelength. Thus, the on-line monitoring for a single microorganism can be realized by detecting and analyzing the corresponding fluorescence signal. The representative advocate of this technology is Jim. Ho (U.S. Pat. No. 5,895,922, Fluorescent biological particle detection system), who achieved a synchronous detection of particle size and fluorescence parameters of a single microorganism in the air using a pulsed laser and subsequently a continuous output semiconductor laser as light sources. However, the particle size data is calculated based on the aerodynamic particle size principle, so that a sheath flow sample injection method is necessary to constrain the air flow to be measured. In addition, the laser must be precisely adjusted to form two parallel beams in the travelling direction of the particles to be measured. Thus, the measurement flow is greatly limited. Also, the system complexity, volume and weight are increased. Jianping Jiang et al. (US patent NO. 20070013910A1, Pathogen and particle detector system and method) use the continuous output semiconductor laser as a light source to achieve a synchronous detection of a scattering particle size of single particle and fluorescence parameters. A forward direction scattered light signal of particles is used to achieve the measurement of particle sizes. An ellipsoidal reflecting mirror is used to receive the fluorescence signals to realized the determination of the biology of single particle. Since the forward direction scattered light of the particle is used as one of the measurement object, and the laser has a stronger energy in the forward direction, further processing such as attenuation, absorption etc. must be applied to the beams to eliminate the impact brought to the scattered light detection. In addition, in this patent, due to the requirement of optical measurement and optical signal collection, the bottom of the ellipsoid should be provided with an opening to enable the air flow to pass through the first focus of the ellipsoidal reflecting mirror. To realize this purpose, the reflecting mirror should have a certain diameter, which has an impact on the miniaturization of the instrument.

SUMMARY OF THE INVENTION

The objectives of the present invention are to overcome the drawbacks of the prior art and provide an aerosol real-time monitor which can realize the on-line monitoring and is portable. The complexity, volume/weight, and the cost of the system is reduced under the condition that the accuracy of the detection is ensured. The technical solution used by the present invention is as follows.

An aerosol real time monitor including:

a laser light source assembly configured to emit a laser beam and generate a line-shaped laser spot at a particle excitation position;

a sealed photoelectric measurement chamber configured to receive an air flow to be measured and form a closed room to prevent light and particles in an external environment from affecting a detection result, wherein the laser light source assembly is assembled at a laser entrance port located at a rear end of the sealed photoelectric measurement chamber and makes an airtight seal of the laser entrance port, and inside the sealed photoelectric measurement chamber, the air flow to be measured intersects a light axis of a traveling direction of the laser beam emitted by the laser light source assembly at the particle excitation position where the line-shaped laser spot located;

a scattered light signal reflecting mirror and a fluorescence signal reflecting mirror bilaterally provided at a left side and a right side with a measurement point as a center, wherein the measurement point is formed by an intersection of the laser beam emitted by the laser light source assembly 100 and the air flow to be measured; a reflection surface of each of the scattered light signal reflecting mirror and the fluorescence signal reflecting mirror is located inside the sealed photoelectric measurement chamber; wherein the scattered light signal reflecting mirror and the fluorescence signal reflecting mirror are respectively configured to collect scattered light and fluorescence generated by exposing the particles to be measured in the air flow to be measured to the laser beam and the scattered light and the fluorescence are respectively reflected to an opposite direction; both the scattered light signal reflecting mirror and the fluorescence signal reflecting mirror are provided with an opening at the center, and the opening is configured to allow the fluorescence and the scattered light reflected from the opposite direction to pass through;

a scattered light signal detector and a fluorescence signal detector respectively mounted behind the opening in the center of the scattered light signal reflecting mirror and the fluorescence signal reflecting mirror to detect a scattered light signal and a fluorescence signal passing through the opening of the reflecting mirrors, respectively;

an extinction reflecting mirror mounted on a laser exit port at a front end of the sealed photoelectric measurement chamber and configured to keep the laser exit port airtight; the extinction reflecting mirror is configured to absorb a part of the laser light and reflect a remaining laser light to a light trap arranged at one side of the extinction reflecting mirror; and the light trap arranged at one side of the extinction reflecting mirror to absorb the remaining laser light.

Further, the laser light source assembly includes a cooling plate, a light source circuit board, a laser diode configured to generate the laser light, a laser diode position adjusting frame, a light source structure fixing block, a spherical mirror, a band-pass emission light filter, a mirror group fixing block, a cylindrical mirror, and an extinction tube; wherein the spherical mirror, the band-pass emission light filter, the cylindrical mirror, and the extinction tube constitute a reshaping mirror group.

The spherical mirror and the band-pass emission light filter are respectively fixed in front of and behind the mirror group fixing block. The mirror group fixing block is arranged inside the light source structure fixing block and the position of the mirror group fixing block can be adjusted along the axis of the laser light. The cylindrical mirror is located right ahead the band-pass emission light filter and is mounted in an outer side of the laser entrance port located in the rear end of the sealed photoelectric measurement chamber. The laser entrance port in front of a mounting position of the cylindrical mirror is provided with a seal ring. The extinction tube is embedded in an inner side of the laser entrance port of the sealed photoelectric measurement chamber and located right ahead the cylindrical mirror. The light source structure fixing block is fixed in an outer side of the rear end of the sealed photoelectric measurement chamber.

the laser diode is soldered to the light source circuit board. The light source circuit board is fixed to the laser diode position adjusting frame. The laser diode position adjusting frame is arranged inside the light source structure fixing block and located in front of the light source circuit board and behind the spherical mirror. The position of the laser diode position adjusting frame can be adjusted in a plane perpendicular to the laser light axis, so that the laser diode and the reshaping mirror group are concentric;

the cooling plate is located behind the light source circuit board and contacts the light source circuit board.

Further, at least two sides of the laser diode position adjusting frame are provided with a jackscrew for adjustment, and the jackscrew is located on the light source structure fixing block.

Further, a head of the laser diode is embedded in the laser diode position adjusting frame.

Further, a vertical direction of the sealed photoelectric measurement chamber is provided with a gas passage including an air inlet joint, an air inlet nozzle, and an air outlet joint. The air inlet joint is tightly screwed to the air inlet nozzle. The air inlet nozzle is fixed to an upper end of the sealed photoelectric measurement chamber. A seal ring is provided for the airtight seal at a fixation position. The air outlet joint is fixed to a lower end of the sealed photoelectric measurement chamber.

Further, the air flow to be measured is orthogonal to the light axis in the travelling direction of the laser beam emitted by the laser light source assembly. The scattered light signal reflecting mirror and the fluorescence signal reflecting mirror are bilaterally, horizontally, and symmetrically placed with the measurement point as a center. The measurement point is formed by an orthogonal intersection of the laser beam emitted by the laser light source assembly and the air flow to be measured. After the air flow to be measured leave the air inlet nozzle, the air flow orthogonally intersects a light axis of the scattered light signal reflecting mirror/fluorescence signal reflecting mirror and a light axis of the travelling direction of the laser light respectively.

Preferably, a front portion of the air inlet nozzle extends into the sealed photoelectric measurement chamber. A closing port of a terminal portion of the air inlet nozzle is flat-round-shaped. A long axis of the closing port is parallel with the light axis in the travelling direction of the laser beam.

Further, the extinction reflecting mirror is mounted on a reflecting mirror fixing holder. The reflecting mirror fixing holder is tightly embedded into the laser exit port in the front end of the sealed photoelectric measurement chamber.

Further, the extinction reflecting mirror is arranged at an angle of 45° with respect to the travelling direction of the laser beam.

Further, a fluorescence signal color filter is provided in front of the fluorescence signal detector.

The advantages of the present invention are as follows.

(1) Since a symmetrical structure of double spherical reflecting mirror is used, one of the double spherical reflecting mirror is used to measure the fluorescence of biological particles, while the other one of the double spherical reflecting mirror is used to measure the scattered light of particles including dust particles and biological particles. Compared with the traditional solution, the structure of the present invention is more compact, easy to be miniaturized, and convenient for installation.

(2) Since the structure of the laser light source assembly is reasonable, the line-shaped laser spot having a single wavelength and concentrated energy can be formed. Moreover, the stray light other than the main spot can be eliminated, so that an effective excitation of the fluorescence of biological particles can be realized.

(3) The concentration and particle size of dust particles and biological particles in the air can be measured.

DETAILED DESCRIPTION OF THE INVENTION

The present invention will be further described with reference to specific drawings and embodiments hereinafter.

Figure 1:
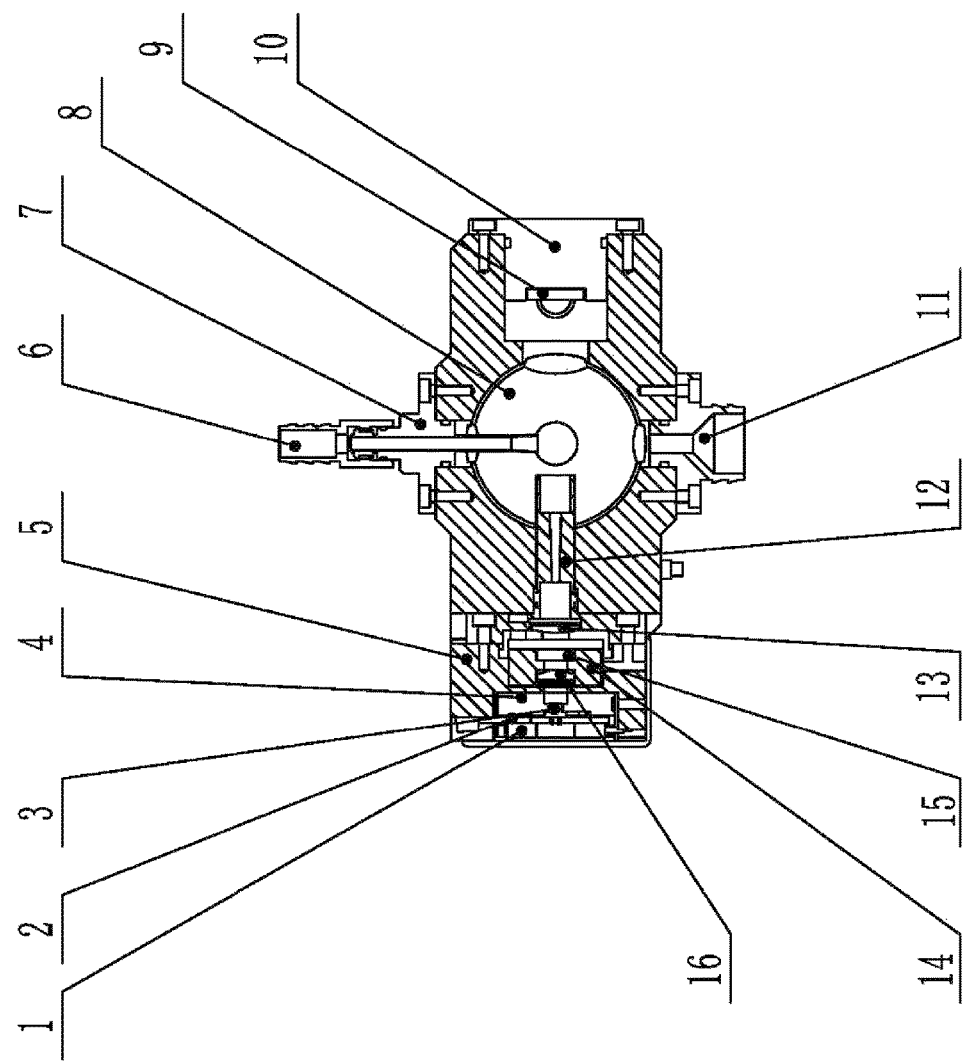
FIG. 1 is a structural schematic view of the present invention.
Figure 2:
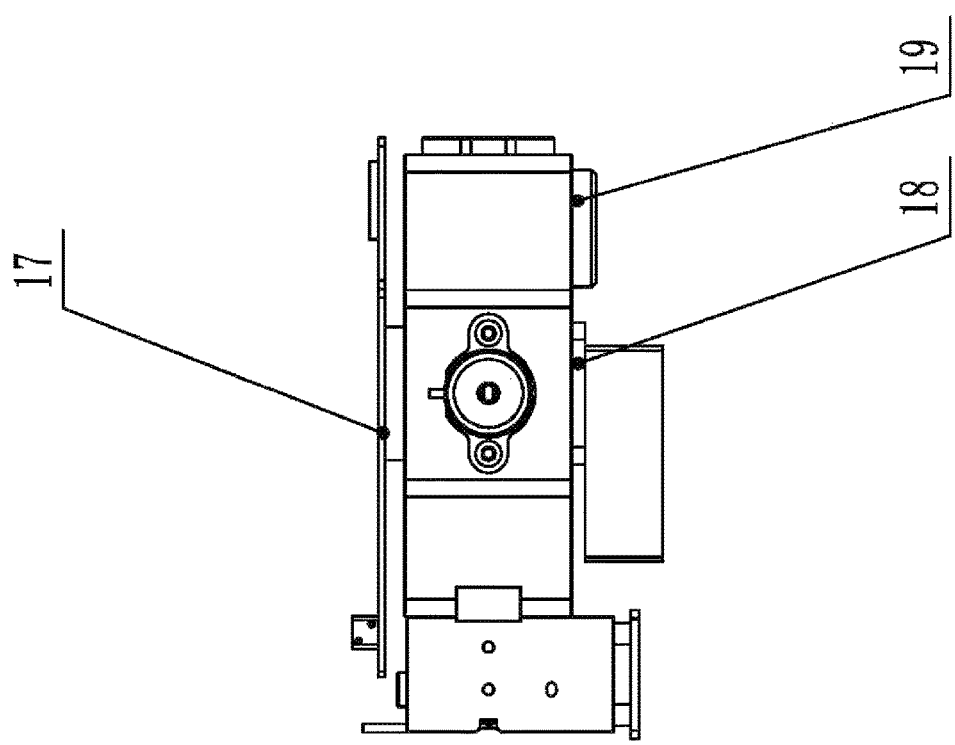
FIG. 2 is a bottom view of FIG. 1.
Figure 3:
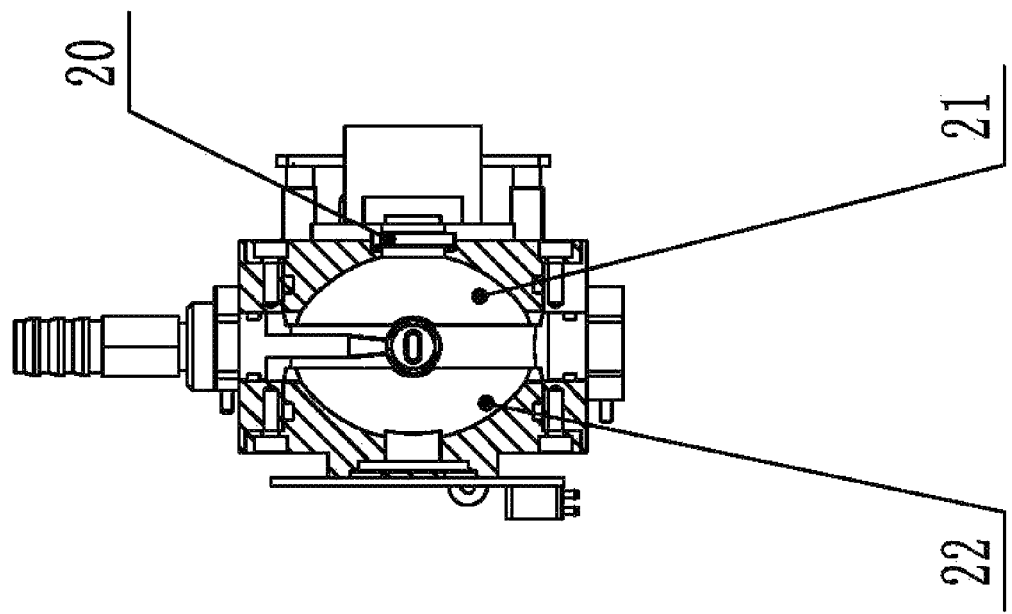
FIG. 3 is a right side view of FIG. 1.
Figure 4:
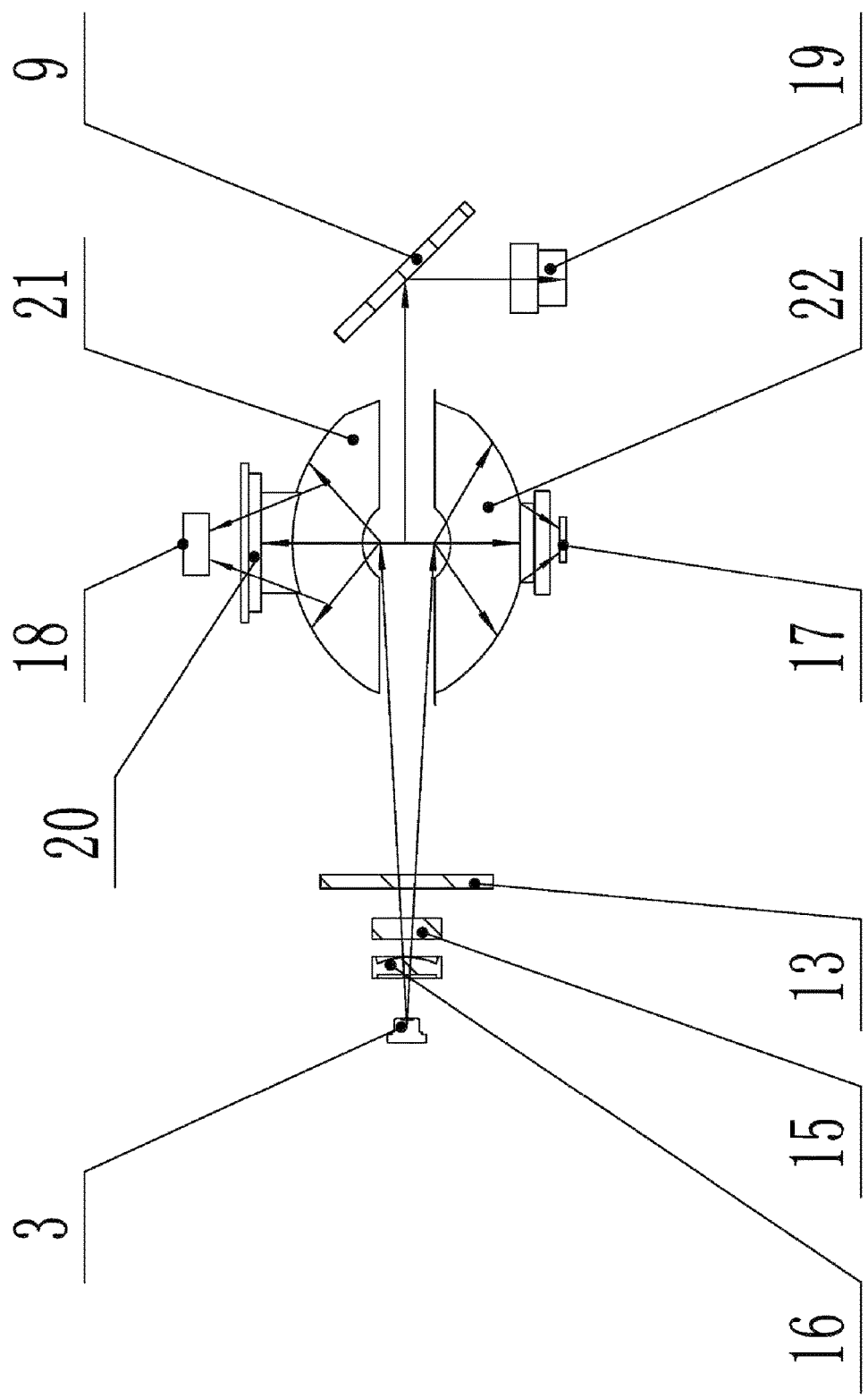
FIG. 4 is a structural schematic view of the gas passage part of the present invention.

The present invention provides an aerosol real-time monitor as shown in FIGS. 1, 2, 3 and 4, which includes laser light source assembly 100, air inlet joint 6, air inlet nozzle 7, sealed photoelectric measurement chamber 8, extinction reflecting mirror 9, reflecting mirror fixing holder 10, air outlet joint 11, scattered light signal detector 17, fluorescence signal detector 18, light trap 19, fluorescence signal color filter 20, scattered light signal reflecting mirror 21, and fluorescence signal reflecting mirror 22 The laser light source assembly 100 includes cooling plate 1, light source circuit board 2, laser diode 3, laser diode position adjusting frame 4, light source structure fixing block 5, spherical mirror 16, band-pass emission light filter 15, mirror group fixing block 14, cylindrical mirror 13, extinction tube 12.

In the laser light source assembly 100, spherical mirror 16, band-pass emission light filter 15, cylindrical mirror 13, and extinction tube 12 constitute a reshaping mirror group. Spherical mirror 16 and band-pass emission light filter 15 are respectively fixed in front of and behind mirror group fixing block 14. Mirror group fixing block 14 is arranged inside light source structure fixing block 5. The position of mirror group fixing block 14 can be axially adjusted along the laser light. An adjustment between mirror group fixing block 14 and light source structure fixing block 5 is realized by adjusting the axial adjustment screw, which is not shown in FIG. 1. Cylindrical mirror 13 is located right ahead band-pass emission light filter 15 and mounted in the outer side of the laser entrance port located in the rear end of sealed photoelectric measurement chamber 8. The laser entrance port which is in front of the mounting position of cylindrical mirror 13 is provided with a seal ring. Extinction tube 12 is embedded into the inner side of the laser entrance port of sealed photoelectric measurement chamber 8 and located right ahead cylindrical mirror 13. A front portion of extinction tube 12 extends into sealed photoelectric measurement chamber 8. Light source structure fixing block 5 is fixed to the outer side of the rear end of sealed photoelectric measurement chamber 8.

Laser diode 3 is soldered to light source circuit board 2. Light source circuit board 2 is fixed to laser diode position adjusting frame 4. Laser diode position adjusting frame 4 is arranged inside light source structure fixing block 5 and located in front of light source circuit board 2 and behind spherical mirror 16. Laser diode position adjusting frame 4 can adjust the position of itself in the plane perpendicular to the laser light axis through the lateral jacketscrew on the light source structure fixing block 5. Accordingly, laser diode 3 and the reshaping mirror group are adjusted to be concentric. Laser diode position adjusting frame 4 is provided with the jacketscrew for adjustment in at least two side directions, wherein there are four side directions i.e. the top, the bottom, the left, and the right.

Cooling plate 1 is located behind light source circuit board 2 and contacts with light source circuit board 2. Cooling plate 1 can be an annular cooling plate.

Light source circuit board 2 is used to supply power to laser diode 3 and used as a heat conduction medium to convey the thermal energy generated during the operation of laser diode 3 to annular cooling plate 1. Laser diode position adjusting block 4 is provided with a space in advance, so that the head of laser diode 3 can be embedded therein with a close fit. The heat generated during the operation of the laser diode can be conveyed to laser diode position adjusting block 4. The divergent laser beams emitted by laser diode 3 firstly pass through spherical mirror 16. Spherical mirror 16 can reshape the divergent laser beams to approximately parallel light. The laser beams being reshaped to approximately parallel light continue to travel forward to pass through band-pass emission light filter 15. Band-pass emission light filter 15 allows the laser light emitted by the laser diode having the ideal wavelength within a selected wavelength range to pass through, while the laser light having other wavelengths are cut off, so that the uniformity of the wavelength of the light source can be ensured. The single-wavelength laser beams reshaped into approximately parallel light continue to travel forward to pass through cylindrical mirror 13. Cylindrical mirror 13 can compress the single-wavelength laser beams reshaped into approximately parallel light, so that a line-shaped laser spot with a concentrated energy density is presented at the position of the particle excitation of the air flow to be measured. Since in the process of laser reshaping, stray light may appear besides the main spot, the signal collection is interfered. Thus, the circuit baseline is shifted up after the photoelectric conversion. The useless small signals are covered. Hence, laser beams would pass through extinction tube 12 after being reshaped by cylindrical mirror 13. The inner wall of the extinction tube 12 is geometrically shaped to block the stray light in the travelling direction, wherein stray light can be eliminated by sawtooth, thread, or matte surface etc. The laser beams are orthogonal to the air flow and continue to travel forward after the particles in the air flow are excited. After that, the laser beams are projected onto the surface of extinction mirror 9, so that most of the laser light are absorbed, and a small part of laser light are reflected to light trap 19 to be absorbed by the light trap. In such a manner, the scattered light interference can be effectively eliminated, such that the signal to noise ratio can be improved.

The position of laser diode position adjustment block 4 can be adjusted in the plane perpendicular to the light axis by a precision adjustment structure. Moreover, laser diode position adjustment block 4 can be fixed after being adjusted to an ideal position. In such a manner, laser diode 3 and the reshaping mirror group can be ensured to be strictly concentric, such that the light source reshape quality is guaranteed. The occurrence of stray light can be reduced. The position of mirror group fixing block 14 can be adjusted in the direction of the light axis by a precision adjustment structure. Mirror group fixing block 14 can be fixed after being adjusted to an ideal position. In such a manner, the convergence position of the laser beams can be adjusted within a certain range, so that the energy of the light spot where the laser beam orthogonally intersects the air flow with particles is the most concentrated. Thus, the efficiency of excitation is improved.

Sealed photoelectric measurement chamber 8 is used to receive the air flow to be measured and form a closed room to prevent the light and particles in the external environment from affecting the detection result. Also, sealed photoelectric measurement chamber 8 further forms a physical support for each of the detection structures. Laser light source assembly 100 is mounted at the laser entrance port located at the rear end of the photoelectric measurement chamber 8 and forms an airtight seal for the laser entrance port. In sealed photoelectric measurement chamber 8, the air flow to be measured is orthogonal to the light axis in the travelling direction of the laser beam emitted by the laser light source assembly at the particle excitation position where the line-shaped laser spot located. Also, if the air flow to be measured is not completely orthogonal to the light axis in the travelling direction of the laser beam emitted by the laser light source assembly, i.e., a certain angle difference occurs with respect to the orthogonal degree of 90, it is also acceptable.

In this embodiment, the air flow to be measured is orthogonal to the light axis in the travelling direction of the laser beam emitted by the laser light source assembly. Thus, gas passage including air inlet joint 6, air inlet nozzle 7, and air outlet joint 11 is arranged in the vertical direction of sealed photoelectric measurement chamber 8. Air inlet joint 6 is tightly screwed to air inlet nozzle 7. Air inlet nozzle 7 is fixed to the upper end of sealed photoelectric measurement chamber 8. A seal ring is embedded into the fixation position for an airtight seal. Air inlet joint 6 and air inlet nozzle 7 form an air inlet gas passage. Air outlet joint 11 is fixed at the lower end of sealed photoelectric measuring chamber 8.

The front portion of air inlet nozzle 7 extends into sealed photoelectric measurement chamber 8 for about 27 mm. The closing end of the rear end of air inlet nozzle 7 is flat-round-shaped. The long axis of the closing end is parallel to the light axis of the travelling direction of the laser beam.

Scattered light signal reflecting mirror 21 and fluorescence signal reflecting mirror 22 are bilaterally, horizontally, and symmetrically placed with the measurement point as a center, wherein the measurement point is formed at the orthogonal intersection of the laser beam emitted by the laser light source assembly 100 and the air flow to be measured. Thus, after the gas (i.e. the air flow to be measured) leave air inlet nozzle 7, the gas orthogonally intersects the light axis of laser light travelling direction, and the light axis of the scattered light signal reflecting mirror 21/fluorescence signal reflecting mirror 22 respectively. Moreover, since the direction of the long axis of the closing end of air inlet nozzle 7 is in consistent with the light axis in the travelling direction of the laser light, more air flow is allowed to pass through the line-shaped laser spot. Therefore, the number of particles to be measured at the laser beam converging position is increased. Moreover, the horizontally symmetric arrangement is not compulsory. Rather, scattered light signal reflecting mirror 21 and fluorescence signal reflecting mirror 22 also can be bilaterally placed with the measurement point as a center, wherein the measurement point is formed at the orthogonal intersection of the laser beam emitted by the laser light source assembly 100 and the air flow to be measured. For example, scattered light signal reflecting mirror 21 and fluorescence signal reflecting mirror 22 are bilaterally placed on the left and right sides of the axis which is at an angle of 30 degrees with respect to the horizontal line passing through the measurement point. In the latter situation, the fixation between scattered light signal reflecting mirror 21 and sealed photoelectric measurement chamber 8, or the fixation between fluorescence signal reflecting mirror 22 and sealed photoelectric measurement chamber 8 may be less convenient than the former situation.

Both scattered light signal reflecting mirror 21 and fluorescence signal reflecting mirror 22 are the spherical mirrors. The rim of each spherical mirror (i.e., an outer edge of an opening) is processed to have a seal ring groove. A close fit is achieved by the seal ring and sealed photoelectric measurement chamber 8. Projections are symmetrically provided above and below the rim of the spherical mirror. Each projection is provided with a threaded hole to accurately fix the spherical mirror in the gas chamber. The reflecting surface of each of scattered light signal reflecting mirror 21 and fluorescence signal reflecting mirror 22 is located inside sealed photoelectric measurement chamber 8. Moreover, scattered light signal reflecting mirror 21 and fluorescence signal reflecting mirror 22 are respectively used to collect a scattered light and a fluorescence generated by exposing the particle to be measured in the air flow to be measured to the laser beam. The scattered light and fluorescence are respectively reflected to an opposite direction. Both scattered light signal reflecting mirror 21 and fluorescence signal reflecting mirror 22 are provided with an opening in the center, which is used for a fluorescence or a scattered light reflected from the opposite direction to pass through.

Scattered light signal detector 17 and fluorescence signal detector 18 are respectively mounted behind the opening at the center of fluorescence signal reflecting mirror 22 and the opening at the center of scattered light signal reflecting mirror 21. Scattered light signal detector 17 and fluorescence signal detector 18 are respectively used to detect the scattered light signal and the fluorescence signal passing through the opening of the reflecting mirror.

The laser beam orthogonally intersects a sample gas of the air flow to be measured entering from air inlet nozzle 7 at the center of sealed photoelectric measurement chamber 8. After being exposed to the laser beams, the particles to be measured in the sample gas emit scattered light and fluorescence. Moreover, the scattered light are reshaped and converged on scattered light signal detector 17 through scattered light signal reflecting mirror 22 fixed on sealed photoelectric measurement chamber 8. Meanwhile, the fluorescence is reshaped and converged on fluorescence signal detector 18 through fluorescence signal reflecting mirror 22. Scattered light signal detector 17 and fluorescence signal detector 18 are provided with corresponding sensors to recognize the interference situation in which the laser light encounters the sample gas to achieve the purpose of detecting the gas particles.

In order to prevent the laser beam from affecting the measurement, extinction mirror 9 is mounted on the laser exit port located at the front end of sealed photoelectric measurement chamber 8. Extinction mirror 9 is the extinction glass. Extinction mirror 9 is mounted on reflecting mirror fixing holder 10. Reflecting mirror fixing holder 10 is hermetically embedded in the laser exit port located in the front end of sealed photoelectric measurement chamber 8. Light trap 19 is mounted on one side of extinction mirror 9 so as to absorb the laser light. Extinction mirror 9 is arranged at an angle of 45° with respect to the travelling direction of the laser beam. The laser beam continues to travel forward after the particles in the air flow are excited. Furthermore, the laser beam is projected onto the surface of the extinction glass, such that most of the laser light is absorbed, and a small part of the laser light is reflected to light trap 19 by the extinction glass and absorbed by the light trap.

More preferably, fluorescence signal color filter 20 is provided in front of fluorescence signal detector 18, so that other light signals other than the fluorescence can be effectively filtered out. Thus, the signal-to-noise ratio of the fluorescence detection is improved.

What is claimed is:

1. An aerosol real time monitor comprising:
   a laser light source assembly, configured to emit a laser beam and generate a line-shaped laser spot at a particle excitation position;
   a sealed photoelectric measurement chamber, configured to receive an air flow to be measured and form a closed room to prevent light and particles in an external environment from affecting a detection result; wherein the laser light source assembly is assembled at a laser entrance port located at a rear end of the sealed photoelectric measurement chamber and makes an airtight seal of the laser entrance port; and inside the sealed photoelectric measurement chamber, the air flow to be measured intersects a light axis of a traveling direction of the laser beam emitted by the laser light source assembly at the particle excitation position where the line-shaped laser spot located;
   a scattered light signal reflecting mirror and a fluorescence signal reflecting mirror, bilaterally provided at a left side and a right side with a measurement point as a center, wherein the measurement point is formed by an intersection of the laser beam emitted by the laser light source assembly 100 and the air flow to be measured; a reflection surface of each of the scattered light signal reflecting mirror and the fluorescence signal reflecting mirror is located inside the sealed photoelectric measurement chamber; wherein the scattered light signal reflecting mirror and the fluorescence signal reflecting mirror are respectively configured to collect scattered light and fluorescence generated by exposing the particles to be measured in the air flow to be measured to the laser beam, and the scattered light and the fluorescence are respectively reflected to an opposite direction; both the scattered light signal reflecting mirror and the fluorescence signal reflecting mirror are provided with an opening at a center, and the opening is configured to allow the fluorescence and a the scattered light reflected from the opposite direction to pass through;

a scattered light signal detector and a fluorescence signal detector, respectively mounted behind the opening in the center of the scattered light signal reflecting mirror and the fluorescence signal reflecting mirror to detect the scattered light signal and the fluorescence signal passing through the opening of the reflecting mirrors, respectively;

an extinction reflecting mirror, mounted on a laser exit port at a front end of the sealed photoelectric measurement chamber, wherein the extinction reflecting mirror is configured to keep the laser exit port airtight; the extinction reflecting mirror is configured to absorb a part of the laser light and reflect a remaining laser light to a light trap arranged at one side of the extinction reflecting mirror; and the light trap, arranged at one side of the extinction reflecting mirror to absorb the remaining laser light.

2. The aerosol real time monitor of claim 1, wherein the laser light source assembly comprises
   a cooling plate,
   a light source circuit board,
   a laser diode configured to generate the laser light,
   a laser diode position adjusting frame,
   a light source structure fixing block,
   a spherical mirror,
   a band-pass emission light filter,
   a mirror group fixing block,
   a cylindrical mirror, and
   an extinction tube;
   wherein
   the spherical mirror, the band-pass emission light filter, the cylindrical mirror, and the extinction tube constitute a reshaping mirror group;
   the spherical mirror and the band-pass emission light filter are respectively fixed in front of and behind the mirror group fixing block;
   the mirror group fixing block is arranged inside the light source structure fixing block, and a position of the mirror group fixing block can be adjusted along the axis of the laser light;
   the cylindrical mirror is located right ahead the band-pass emission light filter and is mounted in an outer side of the laser entrance port located at the rear end of the sealed photoelectric measurement chamber;
   the laser entrance port in front of a mounting position of the cylindrical mirror is provided with a seal ring;
   the extinction tube is embedded in an inner side of the laser entrance port of the sealed photoelectric measurement chamber and located right ahead the cylindrical mirror;
   the light source structure fixing block is fixed in an outer side of the rear end of the sealed photoelectric measurement chamber;
   the laser diode is soldered to the light source circuit board;
   the light source circuit board is fixed to the laser diode position adjusting frame;
   the laser diode position adjusting frame is arranged inside the light source structure fixing block;
   the laser diode position adjusting frame is located in front of the light source circuit board and behind the spherical mirror;
   a position of the laser diode position adjusting frame can be adjusted in a plane perpendicular to the light axis of the laser light, so that the laser diode and the reshaping mirror group are concentric; and
   the cooling plate is located behind the light source circuit board and contacts the light source circuit board.

3. The aerosol real time monitor of claim 2, wherein
at least two sides of the laser diode position adjusting frame are provided with a jackscrew for adjustment; and
the jackscrew is located on the light source structure fixing block.

4. The aerosol real time monitor of claim 3, wherein
a vertical direction of the sealed photoelectric measurement chamber is provided with
a gas passage including an air inlet joint,
an air inlet nozzle, and
an air outlet joint;
wherein
the air inlet joint is tightly screwed to the air inlet nozzle;
the air inlet nozzle is fixed to an upper end of the sealed photoelectric measurement chamber;
a seal ring is provided for the airtight seal at a fixation position; and
the air outlet joint is fixed to a lower end of the sealed photoelectric measurement chamber.

5. The aerosol real time monitor of claim 2, wherein
a head of the laser diode is embedded in the laser diode position adjusting frame.

6. The aerosol real time monitor of claim 5, wherein
a vertical direction of the sealed photoelectric measurement chamber is provided with
a gas passage including an air inlet joint,
an air inlet nozzle, and
an air outlet joint;
wherein
the air inlet joint is tightly screwed to the air inlet nozzle;
the air inlet nozzle is fixed to an upper end of the sealed photoelectric measurement chamber;
a seal ring is provided for the airtight seal at a fixation position; and
the air outlet joint is fixed to a lower end of the sealed photoelectric measurement chamber.

7. The aerosol real time monitor of claim 2, wherein
a vertical direction of the sealed photoelectric measurement chamber is provided with
a gas passage including an air inlet joint,
an air inlet nozzle, and
an air outlet joint;
wherein
the air inlet joint is tightly screwed to the air inlet nozzle;

the air inlet nozzle is fixed to an upper end of the sealed photoelectric measurement chamber;

a seal ring is provided for the airtight seal at a fixation position; and the air outlet joint is fixed to a lower end of the sealed photoelectric measurement chamber.

8. The aerosol real time monitor of claim 1, wherein a vertical direction of the sealed photoelectric measurement chamber is provided with a gas passage including an air inlet joint, an air inlet nozzle, and an air outlet joint;

wherein the air inlet joint is tightly screwed to the air inlet nozzle;

the air inlet nozzle is fixed to an upper end of the sealed photoelectric measurement chamber;

a seal ring is provided for the airtight seal at a fixation position; and the air outlet joint is fixed to a lower end of the sealed photoelectric measurement chamber.

9. The aerosol real time monitor of claim 8, wherein the air flow to be measured is orthogonal to the light axis of the travelling direction of the laser beam emitted by the laser light source assembly;

the scattered light signal reflecting mirror and the fluorescence signal reflecting mirror are bilaterally, horizontally, and symmetrically placed in the left side and the right side with the measurement point as a center;

the measurement point is formed by an orthogonal intersection of the laser beam emitted by the laser light source assembly and the air flow to be measured;

after the air flow to be measured leave the air inlet nozzle, the air flow orthogonally intersects a light axis of the scattered light signal reflecting mirror/fluorescence signal reflecting mirror and a light axis of the travelling direction of the laser light respectively.

10. The aerosol real time monitor of claim 8, wherein a front portion of the air inlet nozzle extends into the sealed photoelectric measurement chamber;

a closing port of a terminal portion of the air inlet nozzle is flat-round-shaped, and a long axis of the closing port is parallel with the light axis in the travelling direction of the laser beam.

11. The aerosol real time monitor of claim 1, wherein the extinction reflecting mirror is mounted on a reflecting mirror fixing holder; and the reflecting mirror fixing holder is tightly embedded into the laser exit port at the front end of the sealed photoelectric measurement chamber.

12. The aerosol real time monitor of claim 1, wherein the extinction reflecting mirror is arranged at an angle of 45° with respect to the travelling direction of the laser beam.

13. The aerosol real time monitor of claim 1, wherein a fluorescence signal color filter is provided in front of the fluorescence signal detector.

* * * * *